US006872860B1

(12) United States Patent
Webb et al.

(10) Patent No.: US 6,872,860 B1
(45) Date of Patent: Mar. 29, 2005

(54) METHOD FOR PRODUCING BISPHENOL CATALYSTS AND BISPHENOLS

(75) Inventors: Jimmy Lynn Webb, Ballston Lake, NY (US); James Lawrence Spivack, Cobleskill, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/626,990

(22) Filed: Jul. 25, 2003

Related U.S. Application Data

(62) Division of application No. 09/954,909, filed on Sep. 18, 2001, now Pat. No. 6,620,939.

(51) Int. Cl.⁷ .............................................. C07C 39/16
(52) U.S. Cl. ..................... 568/728; 502/62; 502/159; 502/162; 502/164; 502/167; 568/727
(58) Field of Search ............................... 568/728, 727; 502/62, 159, 162, 164, 167

(56) References Cited

U.S. PATENT DOCUMENTS

| | | |
|---|---|---|
| 2,607,776 A | 8/1952 | Vinton |
| 2,667,489 A | 1/1954 | Fincke |
| 2,775,620 A | 12/1956 | Williamson |
| 2,831,799 A | 4/1958 | Coouradt et al. |
| 3,037,052 A | 5/1962 | Bortnick et al. |
| 3,049,568 A | 8/1962 | Apel et al. |
| 3,153,001 A | 10/1964 | Apel et al. |
| 3,172,916 A | 3/1965 | Wagner et al. |
| 3,198,847 A | 8/1965 | Lanning |
| 3,242,219 A | 3/1966 | Farnham et al. |
| 3,367,979 A | 2/1968 | Harper et al. |
| 3,394,089 A | 7/1968 | McNutt et al. |
| 3,634,341 A | 1/1972 | Gammill et al. |
| 3,639,663 A | 2/1972 | Ayad et al. |
| 3,651,080 A | 3/1972 | Doebel et al. |
| 3,760,006 A | 9/1973 | Gammill et al. |
| 4,036,974 A | 7/1977 | Walker et al. |
| 4,045,379 A | 8/1977 | Kwantes et al. |
| 4,051,079 A | 9/1977 | Melby |
| 4,053,522 A | 10/1977 | McClure et al. |
| 4,059,705 A | 11/1977 | Walker |
| 4,122,048 A | 10/1978 | Buchwalder et al. |
| 4,123,542 A | 10/1978 | Walker |
| 4,126,618 A | 11/1978 | Winter et al. |
| 4,177,350 A | 12/1979 | Zimgibl et al. |
| 4,191,843 A | 3/1980 | Kwantes et al. |
| 4,239,919 A | 12/1980 | Hairston |
| 4,294,995 A | 10/1981 | Faler et al. |
| 4,308,404 A | 12/1981 | Kwantes et al. |
| 4,308,405 A | 12/1981 | Kwantes |
| 4,315,023 A | 2/1982 | Partyka et al. |
| 4,346,247 A | 8/1982 | Faler et al. |
| 4,365,099 A | 12/1982 | Faler et al. |
| 4,369,293 A | 1/1983 | Heydenreich et al. |
| 4,391,997 A | 7/1983 | Mendiratta |
| 4,396,728 A | 8/1983 | Faler |

(Continued)

FOREIGN PATENT DOCUMENTS

| | | |
|---|---|---|
| EP | 0 171 758 B1 | 8/1985 |
| EP | 0 243 546 A1 | 5/1986 |
| EP | 0 268 318 A1 | 10/1987 |
| EP | 0 421 210 A2 | 9/1990 |
| EP | 0 567 107 A1 | 4/1993 |
| EP | 0 552 518 B1 | 9/1995 |
| EP | 1 160 229 A1 | 12/2001 |
| EP | 1 371 623 A1 | 12/2003 |
| JP | 11-179210 | 7/1999 |
| JP | 11-246458 | 9/1999 |
| WO | WO 97/08122 | 3/1997 |
| WO | WO 01/49640 | 7/2001 |

OTHER PUBLICATIONS

Patent Abstracts of Japan: Japanese Publication No. 2000–128819 Dated May 9, 2000.
Patent Abstracts of Japan: Japanese Publication No. 2000–281608 Dated Oct. 10, 2000.
Patent Abstracts of Japan: Japanese Publication No. 2001–286770 Dated Oct. 16, 2000.
Patent Abstracts of Japan: Japanese Publication No. 2001–288132 Dated Oct. 16, 2001.
Patent Abstracts of Japan: Japanese Publication No. 2002–226417 Dated Aug. 14, 2002.
Patent Abstracts of Japan: Japanese Publication No. 2002–255880 Dated Sep. 11, 2002.
Patent Abstracts of Japan: Japanese Publication No. 2003–055286 Dated Feb. 26, 2003.
Patent Abstracts of Japan: Japanese Publication No. 2003–190805 Dated Jul. 8, 2003.
Patent Abstracts of Japan: Japanese Publication No. 2003–226661 Dated Aug. 12, 2003.
Patent Abstracts of Japan: Japanese Publication No. 2003–246760 Dated Sep. 2, 2003.
Patent Abstracts of Japan: Japanese Publication No. 08–038910 Dated Feb. 13, 1996.
Patent Abstracts of Japan: Japanese Publication No. 08–325185 Dated Dec. 10, 1996.
Patent Abstracts of Japan: Japanese Publication No. 05–294875 Dated Nov. 9, 1993.
Patent Abstracts of Japan: Japanese Publication No. 05–294876 Dated Nov. 9, 1993.
Patent Abstracts of Japan: Japanese Publication No. 05–271132 Dated Oct. 19, 1993.
Patent Abstracts of Japan: Japanese Publication No. 10–314595 Dated Dec. 2, 1998.
Patent Abstracts of Japan: Japanese Publication No. 10–328573 Dated Dec. 15, 1998.
Patent Abstracts of Japan: Japanese Publication No. 11–124351 Dated May 11, 1999.

(Continued)

Primary Examiner—Michael L. Shippen
(74) Attorney, Agent, or Firm—Cantor Colburn LLP

(57) ABSTRACT

This disclosure relates to a method for producing and using catalysts in the production of bisphenols, and in particular to a method for producing catalysts which contain poly-sulfur mercaptan promoters, and using these catalysts in the production of bisphenol-A and its derivatives.

27 Claims, No Drawings

U.S. PATENT DOCUMENTS

| | | |
|---|---|---|
| 4,400,555 A | 8/1983 | Mendiratta |
| 4,419,495 A | 12/1983 | Davis |
| 4,423,252 A | 12/1983 | Maki et al. |
| 4,424,283 A | 1/1984 | Faler et al. |
| 4,439,545 A | 3/1984 | Aspisi et al. |
| 4,448,899 A | 5/1984 | Hass |
| 4,455,409 A | 6/1984 | Faler et al. |
| 4,478,956 A | 10/1984 | Maki et al. |
| 4,496,667 A | 1/1985 | Reichgott et al. |
| 4,535,084 A | 8/1985 | Lombardino et al. |
| 4,549,900 A | 10/1985 | Kramer et al. |
| 4,579,857 A | 4/1986 | Sherlock |
| 4,579,862 A | 4/1986 | Manley et al. |
| 4,584,383 A | 4/1986 | Parhi |
| 4,584,416 A | 4/1986 | Pressman et al. |
| 4,590,303 A | 5/1986 | Mendiratta |
| 4,595,704 A | 6/1986 | Fazio |
| 4,822,923 A | 4/1989 | Li |
| 4,825,010 A | 4/1989 | Li |
| 4,826,849 A | 5/1989 | Heinemann et al. |
| 4,859,803 A | 8/1989 | Shaw |
| 5,100,460 A | 3/1992 | Desbordes et al. |
| 5,141,966 A | 8/1992 | Porath |
| 5,206,131 A | 4/1993 | Matsuda et al. |
| 5,212,206 A | 5/1993 | Rudolph et al. |
| 5,284,981 A | 2/1994 | Rudolph et al. |
| 5,296,609 A | 3/1994 | McCort et al. |
| 5,414,151 A | 5/1995 | Pressman et al. |
| 5,414,152 A | 5/1995 | Cipullo |
| 5,428,075 A | 6/1995 | Pressman et al. |
| 5,436,344 A | 7/1995 | Quallich |
| 5,589,517 A | 12/1996 | Sugawara et al. |
| 5,618,778 A | 4/1997 | Wirth et al. |
| 5,700,943 A | 12/1997 | Daines |
| 5,756,781 A | 5/1998 | Sybert et al. |
| 5,780,690 A | 7/1998 | Berg et al. |
| 5,785,823 A | 7/1998 | Meurer et al. |
| 5,786,373 A | 7/1998 | Hartman et al. |
| 5,789,628 A | 8/1998 | Auer et al. |
| 5,914,431 A | 6/1999 | Fennhoff |
| 5,929,249 A | 7/1999 | Hill et al. |
| 5,932,731 A | 8/1999 | Goda et al. |
| 5,939,494 A | 8/1999 | Wehmeyer et al. |
| 5,973,103 A | 10/1999 | Silva et al. |
| 6,013,845 A | 1/2000 | Allan et al. |
| 6,020,385 A | 2/2000 | Halle et al. |
| 6,114,539 A | 9/2000 | Jautelat et al. |
| 6,133,190 A | 10/2000 | Wehmeyer et al. |
| 6,133,486 A | 10/2000 | Maas et al. |
| 6,150,307 A | 11/2000 | Camenzind et al. |
| 6,211,417 B1 | 4/2001 | Fengler et al. |
| 6,229,037 B1 | 5/2001 | Okubo et al. |
| 6,265,409 B1 | 7/2001 | Cheshire et al. |
| 6,288,284 B1 | 9/2001 | Eek et al. |
| 6,329,556 B1 | 12/2001 | Sakura et al. |
| 6,414,199 B1 | 7/2002 | Saruwatari |
| 6,414,200 B1 | 7/2002 | Spivack et al. |
| 6,534,686 B1 | 3/2003 | Webb et al. |
| 2002/0123656 A1 | 9/2002 | Spivack |
| 2003/0096939 A1 | 5/2003 | Bodiger et al. |
| 2003/0153792 A1 | 8/2003 | Iwahara et al. |

OTHER PUBLICATIONS

Patent Abstracts of Japan: Japanese Publication No. 11–179210 Dated Jul. 6, 1999.
Patent Abstracts of Japan: Japanese Publication No. 11–246458 Dated Sep. 14, 1999.
Patent Abstracts of Japan: Japanese Publication No. 2002–255879 Dated Sep. 11, 2002.
Patent Abstracts of Japan: Japanese Publication No. 2002–255881 Dated Sep. 11, 2002.
Patent Abstracts of Japan: Japanese Publication No. 2002–265402 Dated Sep. 18, 2002.
Patent Abstracts of Japan: Japanese Publication No. 2002–265403 Dated Sep. 18, 2002.
Patent Abstracts of Japan: Japanese Publication No. 2002–316962 Dated Oct. 31, 2002.
Patent Abstracts of Japan: Japanese Publication No. 11–255748 Dated Sep. 21, 1999.
Patent Abstracts of Japan: Japanese Publication No. 10–211434 Dated Aug. 11, 1998.
Patent Abstracts of Japan: Japanese Publication No. 10–218814 Dated Aug. 18, 1998.
Patent Abstracts of Japan: Japanese Publication No. 57–085335 Dated May 28, 1982.
EP 0249102 A3; Publication Date Dec. 16, 1987 (DE 3619450) Abstract Only.
FR 2685323; Publication Date Jun. 25, 1993 Abstract Only.
FR 2685221 Publication Date Jun. 25, 1993 Abstract Only.
EP 0166696 Publication Date Jan. 2, 1986 English Abstract (non–translated patent included).
DE 19834951 Publication Date Feb. 11, 1999 English Abstract (non–translated patent included).
Chemical Abstract No. XP002195035 abstract for JP 08 325185 A (Dec. 10, 1996).
Chemical Abstract No. XP002262268 abstract for "Preparation of lubricating oil additives from dimercaptothiadiazole" Journal of Industrial Engineering Chemistry, vol. 49, 1957.
Chemical Abstract No. XP002132228 (Nov. 19, 1990) abstract for JP 02 167268 A (Jun. 27, 1990).
Chemical Abstract No. XP002271236 abstract for "Characteristics of the reaction of hemolytic and ionic addition of thiols to different vinyl derivatives of some imidazolethiones" Tezisy Dok. Nauchn. Sess. Khim. Tekhnol. Org. Soedin. Sery Sernistykh Neftei, $14^{th}$ (1976).
Chemical Abstract No. XP002262269 abstract for "Polydentate SNXM (X=S,O,N) ligands by selective reduction of organosulfur heterocycles with tributyltin hydride" Phosphorus, Sulfur and Silicon and the Related Elements (1996).
Chemical Abstract No. XP002271237 abstract for "Syntheses based on mercaptobenzothiazole, mercaptobenzoxazole and mercaptobenzimidazole. II. Reactions for 2–benzoxazolyl vinyl sulfide and 2–benzimidazolyl vinyl sulfide" Izvestiya Akademii Nauk SSSR, Seriya Khimicheskaya (1969).
Chemical Abstract No. XP002271238 abstract for "Behavior of N,S–divinyl–2–mercaptobenzimidazole in a thiolation reaction" Khimiya Geterotsiklicheskikh Soedinenii (1975).
Chemical Abstract, vol. 66, No. 13, Mar. 27, 1967, No. XP002132227 abstract for "Syntheses based on 2–benzothiazolyl vinyl sulfide" Zhurnal Organiceskoi Khimii (1966).
Chemical Abstract No. XP002271239 abstract for "Determination of urinary 2–mercaptobenzothiazole (2–MBT), the main metabolite of 2–(thiocyanomethylthio) benzothiazole (TCMTB) in humans and rats" Archives of Toxicology (1996).

Chemical Abstract No. XP002271240 abstract for "Radical addition of thiols to vinyl derivatives for 4,5–diphenylimidazole—2– thione" Khimiya Geterotsiklicheskikh Soedinenii (1976).

Chemical Abstract No. XP002271241 abstract for "Synthesis of a new class of polydentate ligands: [bis(2–imidazolyl)methyl]amino–thioether–thiols" Inorganica Chimica Acta (1984).

Sellmann et al. "Transition metal complexes with sulfur ligands. 136.[1] enforced trans coordination of thiolate donors in electron rich iron, ruthenium, and nickel [M(L)(pyN$_2$H$_2$S$_2$)] and [M(L)(pyS$_4$)] complexes (L=CO, PPh$_3$, DMSO) (pyN$_2$H$_2$S$_2{}^{2-}$=2,6–Bis(2–mercaptophenylamino)dimethylpyridine(2–); pyS$_4{}^{2-}$=2,6–Bis(2–mercaptophenylthio)dimethylpyridine(2–))" Inorg. Chem. 1999, 38, 5314–5322.

Nekola et al. "Thiofunctional Vanadium Complexes" Inorg. Chem., 2002, 41, 2379–2384.

Japanese Patent Abstract for 02108039 A Application Date Oct. 18, 1988.

Japanese Patent Abstract for JP 04063301 A Application Date Jul. 03, 1990.

METHOD FOR PRODUCING BISPHENOL CATALYSTS AND BISPHENOLS

CROSS-REFERENCE TO RELATED APPLICATIONS

This application is a divisional of U.S. application Ser. No. 09/954,909, filed Sep. 18, 2001, now U.S. Pat. No. 6,620,939, the entire contents of which are hereby incorporated by reference.

BACKGROUND OF THE INVENTION

This disclosure relates to a method for producing and using catalysts for the production of bisphenols, and in particular to a method for producing catalysts which contain attached poly-sulfur mercaptan promoters, and using these catalysts in the production of bisphenol-A, and its derivatives.

Typical bisphenols, such as 4,4'-isopropylidenediphenol, e.g., bisphenol-A (BPA), are widely employed as monomers in the manufacture of polymeric materials, such as engineering thermoplastics. For example, BPA is a principal monomer used in the manufacture of polycarbonate. Bisphenols are generally prepared by the electrophilic addition of aldehydes, or ketones such as acetone, to aromatic hydroxy compounds such as phenol, in the presence of an acidic catalyst compositions. These types of reactions are also referred to as acid catalyzed condensation reactions. Commercially, sulfonated polystyrene resin cross-linked with divinylbenzene, e.g., PS-DVB, is typically used as a solid acid component of the catalyst composition. Reaction promoters can also be employed as part of a catalyst composition to improve the reaction rate, and selectivity, of the desired condensation reaction; in the case of BPA, the desired selectivity is for the para-para isomer (pp-BPA). Promoters can be present as unattached molecules in the bulk reaction matrix, e.g., "bulk-promoters", or can be attached to the resin through ionic linkages, e.g., "attached-promoters". A useful class of promoter is the mercaptans, specifically thiols, e.g., organosulfur compounds which are derivatives of hydrogen sulfide. Typical mercaptan promoters contain only a single sulfur atom, and result in catalyst compositions that catalyze bisphenol formation with poor isomer selectivity; in the case of BPA, the undesired selectivity if for the ortho-para isomer (op-BPA). Consequently, a long felt yet unsatisfied need exists for new and improved catalyst compositions, and a method to produce them, which are selective in the production of bisphenols. Herein, a method to produce catalyst compositions comprising poly-sulfur mercaptan promoters is disclosed. The use of poly-sulfur mercaptan promoters results in catalyst compositions that are highly selective in the formation of bisphenols.

SUMMARY OF THE INVENTION

In one embodiment, the present disclosure pertains to a method for producing a catalyst composition which catalyzes the formation of bisphenols from aromatic hydroxy compounds and carbonyl containing compounds, said method comprising the step of attaching a poly-sulfur mercaptan promoter component to a solid acid support component comprising a protic acid functionality, said poly-sulfur mercaptan promoter component having the following structure (I),

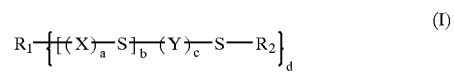

wherein $R_1$ is a functionality selected from the group consisting of a positively charged ammonium functionality, a positively charged guanidinium functionality, a positively charged phosphonium functionality, and a neutral amine;
wherein a is between about 0 and about 11;
wherein b is between about 1 and about 11;
wherein c is between about 1 and about 11;
wherein d is between about 1 and about 5;
wherein X is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms;
wherein Y is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms; and
wherein $R_2$ is one member selected from the group consisting of a hydrogen, a tertiary aliphatic functionality, an ester functionality, a carbonate functionality, and a benzyl functionality which is attached via the benzylic methylene carbon.

In another embodiment, the present disclosure relates to a method for forming bisphenols, comprising the step of reacting an aromatic hydroxy compound with a carbonyl containing compound in the presence of a catalyst composition, said catalyst composition comprising a solid acid component and a poly-sulfur mercaptan promoter component having the following structure (I),

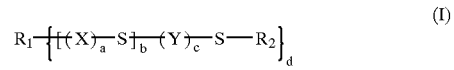

wherein $R_1$ is a functionality selected from the group consisting of a positively charged ammonium functionality, a positively charged guanidinium functionality, a positively charged phosphonium functionality, and a neutral amine;
wherein a is between about 0 and about 11;
wherein b is between about 1 and about 11;
wherein c is between about 1 and about 11;
wherein d is between about 1 and about 5;
wherein X is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms;
wherein Y is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms; and wherein $R_2$ is one member selected from the group consisting of a hydrogen, a tertiary aliphatic functionality, an ester functionality, a carbonate functionality, and a benzyl functionality which is attached via the benzylic methylene carbon.

DETAILED DESCRIPTION

The present disclosure is directed to a method for producing and using catalysts for the production of bisphenols, and is suitable for the preparation of attached-promoter catalysts, which can effectively catalyze the formation of bisphenols from aromatic hydroxy compounds and carbonyl containing compounds. In the context of the present disclosure, the term "catalyst" refers to a composition, wherein the individual constituents of the composition are referred to as "components". In the context of the present disclosure, a typical catalyst comprises a "support" component that is generally a polymeric material, also referred to as a "resin", comprising a protic acid functionality, and a "promoter" component that is generally an organic compound. As used herein, the term "functionality" is defined as an atom, or group of atoms acting as a unit, whose presence imparts characteristic properties to the molecule to which the functionality is attached. In the context of the present disclosure, a "protic acid functionality" is defined as a group of atoms that are covalently attached to the polymeric support component of the catalyst, which can act as a source of protons, e.g., a Bronsted acid, and upon deprotonation the counter-anion can serve as an anionic moiety of an ionic bond with a cationically charged promoter component. A suitable example of a support component is a polystyrene resin, cross-linked with up to 12 percent of divinylbenzene. Suitable examples of protic acid functionalities, which are attached to the support component, are a sulfonic acid functionality, which upon deprotonation produces a sulfonate anion functionality, a phosphonic acid functionality, which upon deprotonation produces a phosphonate anion functionality, and a carboxylic acid functionality, which upon deprotonation produces a carboxylate anion functionality. For example, in one embodiment of the present disclosure, the support component is a polystyrene resin, cross-linked with 4% of divinylbenzene, and functionalized with sulfonic acid groups.

Promoter components are typically organic compounds, which can readily form stable cationic species. Typical promoter components comprise at least one mercaptan chain functionality, and an organic skeletal functionality, to which the mercaptan chain functionality is covalently bound. As used herein, the term "mercaptan chain functionality" is defined as an organosulfur functionality, which is a derivative of hydrogen sulfide. In the context of the present disclosure, a typical mercaptan chain functionality, i.e. —{[(X)$_a$—S]$_b$—(Y)$_c$—S—R), comprises at least two (2) sulfur atoms. In one embodiment up to twelve sulfur atoms can be present in a single mercaptan chain, e.g., b is between about 1 and about 12 in a chain defined by the following formula, —{[(X)$_a$—S]$_b$—(Y)$_c$—S—R}. The sulfur atoms in a typical mercaptan chain functionality are linked by various organic linkers functionalities, e.g., X and Y. In the context of the present disclosure, typical linker functionalities include, but are not limited to, a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms. The term "organic skeletal functionality" is defined as an organic functionality, which is capable of forming a covalent bond with at least one mercaptan chain functionality, and can form a stable cationic species that can act as a cationic moiety of an ionic bond. Suitable examples of organic skeletal functionalities include, but are not limited to, an alkylammonium functionality, an alkylguanidinium functionality, an alkylphosphonium functionality, and an amino functionality. Typically amino skeletal functionalities include, but are not limited to, monocyclic aromatic amino compounds, and polycyclic aromatic amino compounds. For example, suitable amino skeletal functionalities include, but are not limited to, pyridyl functionalities, benzimidazole functionalities, benzothiazole functionalities, and imidazole functionalities. In the case of skeletal functionalities that comprise ring systems, a mercaptan chain functionality can be bonded to the ring system at any one of the ring locations that is capable of covalently bonding a substituent. For example, in the case of a pyridyl-mercaptan promoter, a mercaptan chain functionality can be appended to pyridine ring at any one of the 2, 3, or 4 ring positions. Furthermore, in each of the classes of mercaptan promoter described above, i.e. alkylammonium mercaptans, alkylguanidinium mercaptans, alkylphosphonium mercaptans, and amino mercaptans, more than one mercaptan chain can be present in the promoter. For example, in the case of pyridyl-mercaptans, the pyridine ring can be substituted with up to 5 mercaptan chain functionalities, with one chain covalently bonded to each of the five carbon ring positions of the pyridine ring.

Substituent groups, which are typically represented by the symbol R in chemical structures, can also be attached to a promoter to adjust the promoter's electronic properties, steric properties, and combinations thereof, to affect the reactivity of the overall catalyst composition. Suitable promoter substituent groups include, but are not limited to, a hydrogen, a fluoride, a bromide, a chloride, an iodide, a vinyl group, a hydroxide, an alkoxide functionality comprising between about 1 and about 11 carbon atoms, an aryloxide functionality comprising at least about 6 carbon atoms, an aliphatic functionality comprising between about 1 and about 11 carbon atoms, and an aromatic functionality comprising at least about 6 carbon atoms. In the case of aminomercaptans that comprise ring systems, a substituent group can also be a cycloaliphatic ring comprising at least about 5 carbon atoms, said cycloaliphatic ring being fused to the amino ring through an adjacent ring substituent, or a cycloaromatic ring comprising at least about 6 carbon atoms, said cycloaromatic ring being fused to the amino ring through an adjacent ring substituent.

Attachment of a promoter component to the polymeric support component is typically made via an ionic linkage between a cationically charged promoter component, which in the case of an aminomercaptan results from the protonation at the nitrogen atom, and the anionically charged deprotonated acid functionality on the resin backbone. The attachment of an aminomercaptan promoter to an acid functionalized polymeric support can be performed in an aqueous solution. Herein, the term "aqueous solution" includes those solutions where water is present as a solvent. For example, a protected mercaptan promoter, such as [2—((CH$_2$)$_2$—S—(CH$_2$)$_3$—S—($^t$—Bu))pyridine], can be attached to a sulfonic acid functionalized PS-DVB resin through an ionic linkage formed between a [2—((CH$_2$)$_2$—S—(CH$_2$)$_3$—S—($^t$—Bu))pyridinium]$^+$ cation, and a sulfonate anion on the polymeric support, by mixing the PS-DVB resin and the mercaptan promoter together in water. Alternatively, the aminomercaptan promoter can be attached to an acid functionalized polymeric support in an organic medium comprising an aromatic hydroxy compound, such as phenol.

In one embodiment of the present disclosure, the mercaptan promoter is protected at the sulfur atom, before it is attached to the support with a typical protecting group functionality used to protect Group 16 elements, such as oxygen and sulfur, from oxidation. As used herein, the term "protecting group" refers to a functionality which inhibits a specific type of reactivity, and in the context of the present disclosure, the protecting group attached to the terminal sulfur atom of the mercaptan promoter is present in order to inhibit the oxidation of the terminal sulfur atom; typically, unprotected mercaptan sulfhydryl groups are readily oxidized to disulfides, or more highly oxidized groups, during synthesis or under the conditions in which the promoters are attached to the polymeric supports. In the context of the present disclosure, suitable examples of sulfur protecting groups include, but are not limited to, aliphatic functionalities that form stable carbocations, ester functionalities, carbonate functionalities, and benzylic functionalities. When used in conjunction with the term protecting group, the term "aliphatic" refers to an organic compound composed of hydrogen atoms and carbon atom arranged in a branched chain, capable of forming a stable carbocation species. For example, in one embodiment the aliphatic protecting group is a tertiary butyl group, e.g., —C(CH$_3$)$_3$. However, when used in conjunction with the term "substituent", the term "aliphatic" refers more broadly to an organic compound composed of hydrogen atoms and carbon atoms which contains between about 1 and about 11 carbon atoms, arranged in either a linear or branched chain. Furthermore, when used in conjunction with the term "substituent", the term "aromatic" is defined as an organic compound composed of hydrogen atoms and carbon atoms, which contains at least about 6 cyclic conjugated carbon atoms.

Suitable examples of ester functionalities, e.g., —C(O)R wherein R can be either an aliphatic substituent or an aromatic substituent, include those esters which contain between about 1 and about 11 carbon atoms, such as an acetate group, e.g., —C(O)CH$_3$. Suitable examples of carbonate functionalities, e.g., —C(O)OR, include carbonates with aliphatic substituents or aromatic substituents. An example of a suitable aliphatic carbonate protecting group is as a tert-butoxy carbonate, e.g., —C(O)O—$^t$Bu. An example of a suitable aromatic carbonate protecting group is as a phenyl carbonate group, e.g., —C(O)OPh. Suitable examples of benzylic functionalities, e.g., —CH$_2$(aryl), include those benzylic groups which contain at least 7 carbon atoms, such as a benzyl group, e.g., —CH$_2$(C$_6$H$_6$).

In one embodiment, the promotor component is

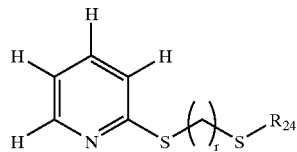

wherein R$_{24}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached via the benzylic methylene carbon; and wherein r is 3 or 6.

In another embodiment, the promoter component is,

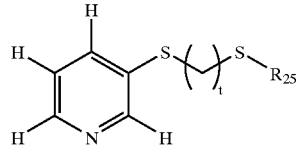

wherein R$_{25}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached via the benzylic methylene carbon; and wherein t is 3 or 6.

In yet another embodiment, the promoter component is

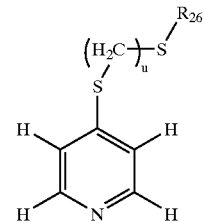

wherein R$_{26}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached via the benzylic methylene carbon; and wherein u is 3 or 6.

In yet another embodiment, the promoter component is

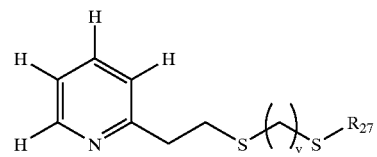

wherein R$_{27}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached via the benzylic methylene carbon; and wherein v is 3 or 6.

In yet another embodiment, the promoter component is,

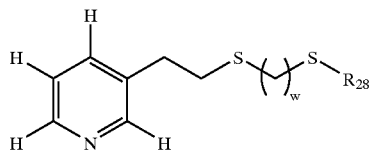

wherein $R_{28}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached via the benzylic methylene carbon; and wherein w is 3 or 6.

In yet another embodiment, the promoter component is

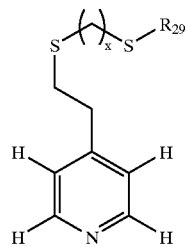

wherein $R_{29}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached via the benzylic methylene carbon; and wherein x is 3 or 6.

In yet another embodiment, the promoter component is,

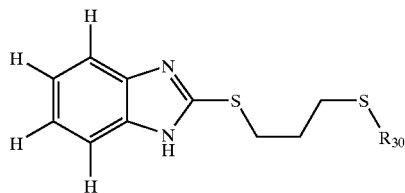

wherein $R_{30}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, land a benzylic functionality comprising at least about 7 carbon atoms which is attached via the benzylic methylene carbon.

In yet another embodiment, the promoter component is,

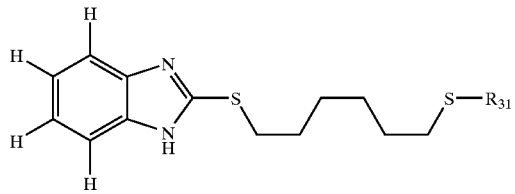

wherein $R_{31}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached via the benzylic methylene carbon.

In yet another embodiment the promoter component is,

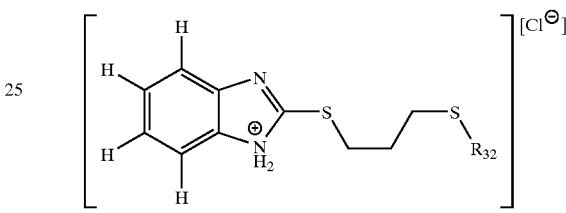

wherein $R_{32}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached via the benzylic methylene carbon.

In yet another embodiment, the promoter component is,

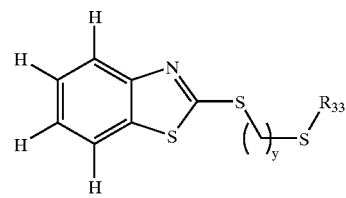

wherein $R_{33}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached via the benzylic methylene carbon; and wherein y is 3 or 6.

In another embodiment, the present application relates to a method for using the catalysts disclosed herein, to catalyze the formation of bisphenols, such as 4,4'-isopropylidenediphenol. In the context of the present disclosure, the term "catalyze", when used in reference to a catalyst composition, refers to the facilitation of a specific chemical transformation between one or more chemical species, at a reaction rate or selectivity, which is greater than, or equal to, a predetermined reference reaction rate, or reference selectivity, under a specific set of reaction conditions. In the context of the present disclosure, the reaction that is being catalyzed is a condensation reaction between an aromatic hydroxy compound and carbonyl-comprising compound to form a bisphenol, which typically occurs in a liquid reaction mixture. Herein, the term "liquid reaction mixture" is defined as a mixture of compounds, which are present predominantly in a liquid state at ambient room temperature and pressure (e.g., about 25° C. and about 0.1 MPa). Liquid reaction mixtures can be homogeneous liquid mixtures composed of one of more phases (e.g., biphasic liquid reaction mixtures), or heterogeneous liquid-solid mixtures comprising components that are present in the solid state (e.g., precipitates).

The components which are present in a typical liquid reaction mixture of a condensation reaction to produce bisphenols include, but are not limited to, the desired bisphenol, byproducts of the condensation reaction such as water, and bisphenols other than the desired bisphenol, soluble components of the catalyst composition, insoluble components of the catalyst composition, and unreacted starting materials, e.g. an aromatic hydroxy compound, and a carbonyl containing compound. Suitable types of aromatic hydroxy compounds include, but are not limited to, monocyclic aromatic compounds comprising at least one hydroxy group, and polycyclic aromatic compounds comprising at least one hydroxy group. Illustrative examples of suitable aromatic hydroxy compounds include, but are not limited to, phenol, alkylphenols, alkoxyphenols, naphthols, alkylnaphthols, and alkoxynaphthols. As used herein, the term "carbonyl containing" compounds refers to organic compounds which contain an $sp^2$ hybridized carbon which is double bonded to an oxygen atom, and includes aldehydes, and ketones. An example of a suitable aldehyde is acetaldehyde. An example of a suitable ketone is acetone.

The condensation reaction can be influenced by various reaction conditions including, but not limited to, reactor vessel pressure, reaction temperature, agitation rate, the pH of the reaction mixture, catalyst concentration, the weight % of various components of the liquid reaction mixture including, but not limited to, the weight % of an aromatic hydroxy compound, the weight % of a carbonyl containing compound, the weight % of a desired bisphenol, and the weight % of water. For example, typical reaction conditions for the catalytic production of BPA using the catalysts described herein and an incremental flow reactor include, but are not limited to, temperatures between about 55° C. and about 85° C., acetone concentrations of between about 1% and about 10%, and space velocities between about 0.1 pounds of feed per pound of solid catalyst per hour and 10 pounds of feed per pound of solid catalyst per hour.

In one embodiment, a method for producing a catalyst composition which catalyzes the formation of bisphenols from aromatic hydroxy compounds and carbonyl containing compounds comprises the step of attaching a poly-sulfur mercaptan promoter component to a solid acid support component comprising a protic acid functionality, wherein the poly-sulfur mercaptan promoter component has the following structure (I),

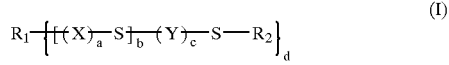
(I)

wherein $R_1$ is a functionality selected from the group consisting of a positively charged ammonium functionality, a positively charged guanidinium functionality, a positively charged phosphonium functionality, and a neutral amine; wherein a is between about 0 and about 11; wherein b is between about 1 and about 11; wherein c is between about 1 B and about 11; wherein d is between about 1 and about 5; wherein X is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms; wherein Y is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms; and wherein $R_2$ is one member selected from the group consisting of a hydrogen, a secondary aliphatic functionality, a tertiary aliphatic functionality, an ester functionality, a carbonate functionality, and a benzyl functionality which is attached via the benzylic methylene carbon.

In the structure (I) above, the tertiary aliphatic functionality is one member selected from the group consisting of a branched aliphatic functionality, and a cyclic aliphatic functionality. Further, the $R_2$ functionality is one member selected from the group consisting of an isopropyl functionality, an isobutyl functionality, a tertiary butyl functionality, a tertiary amyl functionality, a cyclopentyl functionality, a benzyl, a 4-methoxybenzyl functionality, a 1-methylcyclohexyl functionality, and a cyclohexyl functionality. The ester functionality is one member selected from the group consisting of an acetate functionality, a propionate functionality, and a benzoate functionality. The carbonate functionality is one member selected from the group consisting of an alkyl carbonate functionality, and an aromatic carbonate functionality.

In an exemplary embodiment, the bisphenol which is being formed is 4,4'-isopropylidenediphenol. The carbonyl containing compound is a ketone or an aldehyde. A preferred carbonyl compound is acetone. A preferred aromatic hydroxy compound is phenol. It is generally desired for the attachment step to be performed in an aqueous solution comprising water. In one embodiment, the solid acid in structure (I) comprises at least one member selected from the group consisting of polystyrene, a zeolite, and silica. In another embodiment, the solid acid is a sulfonic acid functionalized polymeric acid, wherein the polymeric resin further comprises divinylbenzene in an amount of up to about 12 wt % of the total weight of the polymeric resin. In another embodiment, the solid acid in structure (I) comprises a protic acid functionality having at least one member selected from the group consisting of a sulfonic acid functionality, a phosphonic acid functionality, and a carboxylic acid functionality.

In one embodiment, a method for producing a catalyst composition which catalyzes the formation of bisphenols from aromatic hydroxy compounds and carbonyl containing compounds comprises the step of attaching a poly-sulfur mercaptan promoter component to a polymeric resin component comprising a protic acid functionality. The functionalized poly-sulfur mercaptan promoter may be a pyridine mercaptan having the following the structure (II),

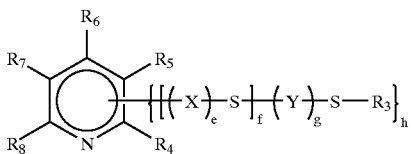

(II)

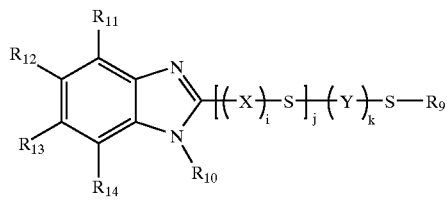

(III)

wherein e is between about 0 and about 11; wherein f is between about 1 and about 11;
wherein g is between about 1 and about 11; wherein h is between about 1 and about 5;
wherein X is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms;
wherein Y is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms; wherein $R_3$ is a hydrogen or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached to the terminal sulfur atom via the benzylic methylene carbon; and wherein at least one member selected from the group consisting of $R_4$, $R_5$, $R_6$, $R_7$, and $R_8$ is a $\{[(X)_eS]_f(Y)_gS-R_3]\}$ chain, and each of $R_4$, $R_5$, $R_6$, $R_7$, and $R_8$ that is not a $\{[(X)_eS]_f(Y)_gS-R_3]\}$ chain is independently one member selected from the group consisting of a hydrogen, a fluoride, a bromide, a chloride, an iodide, a vinyl group, a hydroxide, an alkoxide functionality comprising between about 1 and about 11 carbon atoms, an aryloxide functionality comprising at least about 6 carbon atoms, an aliphatic functionality comprising between about 1 and about 11 carbon atoms, an aromatic functionality comprising at least about 6 carbon atoms, a cycloaliphatic ring comprising at least about 5 carbon, said cycloaliphatic ring being fused to the pyridine ring through an adjacent ring substituent, and a cycloaromatic ring comprising at least about 6 carbon atoms, said cycloaromatic ring being fused to the pyridine ring through an adjacent ring substituent. In one embodiment in the structure (II) above, X is a —CH$_2$— group, e is 2, f is 1, Y is a —CH$_2$— group, g is 3, and $R_4$ is the $\{[(X)_eS]_f(Y)_gS-R_3]\}$ chain in structure. In another embodiment in the structure (II) above, X is a —CH$_2$— group, e is 2, f is 1, Y is a —CH$_2$— group, g is 3, and $R_5$ is the $\{[(X)_eS]_f(Y)_gS-R_3]\}$ chain. In yet another embodiment in the structure (II) above, X is a —CH$_2$— group, e is 2, f is 1, Y is a —CH$_2$— group, g is 3, and $R_6$ is the $\{[(X)_eS]_f(Y)_gS-R_3]\}$ chain.

In one embodiment, the poly-sulfur mercaptan promoter component is a functionalized benzimidazole mercaptan, wherein the functionalized benzimidazole mercaptan has the structure (III), wherein l is between about 0 and about 11; wherein j is between about 1 and about 11; wherein k is between about 1 and about 11; wherein $R_9$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached to the terminal sulfur atom via the benzylic methylene carbon; wherein $R_{10}$ is one member selected from the group consisting of a hydrogen, an aliphatic carbonyl functionality comprising about 1 to about 11 carbon atoms, an aliphatic functionality comprising between about 1 and about 11 carbon atoms, an aromatic carbonyl functionality comprising at least about 7 carbon atoms, and an aromatic functionality comprising at least about 6 carbon atoms; and wherein each of $R_{11}$, $R_{12}$, $R_{13}$ and $R_{14}$ are independently one member selected from the group consisting of a hydrogen, a fluoride, a bromide, a chloride, an iodide, a vinyl group, a hydroxide, an alkoxide functionality comprising between about 1 and about 11 carbon atoms, an aryloxide functionality comprising at least about 6 carbon atoms, an aliphatic functionality comprising between about 1 and about 11 carbon atoms, an aromatic functionality comprising at least about 6 carbon atoms, a cycloaliphatic ring comprising at least about 5 carbon atoms, said cycloaliphatic ring being fused to the benzimidazole arene ring through an adjacent ring substituent, and a cycloaromatic ring comprising at least about 6 carbon atoms, said cycloaromatic ring being fused to the benzimidazole arene ring through an adjacent ring substituent.

In another embodiment, the poly-sulfur mercaptan promoter component is a functionalized benzothiazole mercaptan, wherein the functionalized benzothiazole mercaptan has the structure (IV),

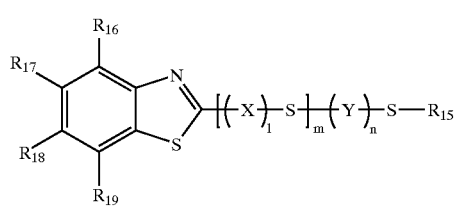

(IV)

wherein l is between about 0 and about 11; wherein m is between about 1 and about 11;
wherein n is between about 1 and about 11; wherein $R_{15}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached to the terminal sulfur atom via the benzylic methylene carbon; and wherein each of $R_{16}$, $R_{17}$, $R_{18}$, and $R_{19}$ are independently one member selected from the group consisting of a hydrogen, a fluoride, a bromide, a chloride, an iodide, a vinyl group, a hydroxide, an alkoxide functionality comprising between about 1 and about 11 carbon atoms, an aryloxide functionality comprising at least about 6 carbon atoms, an aliphatic functionality comprising between about 1 and about 11 carbon atoms, an aromatic functionality comprising at least about 6 carbon atoms, a cycloaliphatic ring comprising at least about 5 carbon atoms, said cycloaliphatic ring being fused to the benzothiazole arene ring through an adjacent ring substituent, and a cycloaromatic ring comprising at least about 6 carbon atoms, said cycloaromatic ring being fused to the benzothiazole arene ring through an adjacent ring substituent.

In another embodiment, the poly-sulfur mercaptan promoter component is a functionalized imidazole mercaptan, wherein the functionalized imidazole mercaptan has the structure (V),

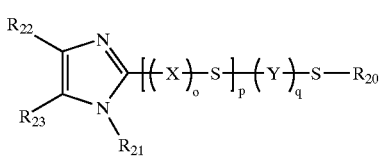

(V)

wherein 0 is between about 0 and about 11; wherein p is between about 1 and about 11;
wherein q is between about 1 and about 11; wherein $R_{20}$ is a hydrogen atom or a sulfur-protecting functionality which is one member selected from the group consisting of an aliphatic functionality comprising at least about 4 carbon atom, an ester functionality comprising between about 1 and about 11 carbon atoms, a carbonate functionality comprising between about 1 and about 11 carbon atoms, and a benzylic functionality comprising at least about 7 carbon atoms which is attached to the terminal sulfur atom via the benzylic methylene carbon; wherein $R_{21}$ is one member selected from the group consisting of a hydrogen, an aliphatic carbonyl functionality comprising about 1 to about 11 carbon atoms, an aliphatic functionality comprising between about 1 and about 11 carbon atoms, an aromatic carbonyl functionality comprising at least about 7 carbon atoms, and an aromatic functionality comprising at least about 6 carbon atoms; and
wherein each of $R_{22}$ and $R_{23}$ are independently one member selected from the group consisting of a hydrogen, a fluoride, a bromide, a chloride, an iodide, a vinyl group, a hydroxide, an alkoxide functionality comprising between about 1 and about 11 carbon atoms, an aryloxide functionality comprising at least about 6 carbon atoms, an aliphatic functionality comprising between about 1 and about 11 carbon atoms, an aromatic functionality comprising at least about 6 carbon atoms, a cycloaliphatic ring comprising at least about 5 carbon atoms, said cycloaliphatic ring being fused to the imidazole ring through an adjacent ring substituent, and a cycloaromatic ring comprising at least about 6 carbon atoms, said cycloaromatic ring being fused to the imidazole ring through an adjacent ring substituent. In one exemplary embodiment, in the structures (I), (II), (III), (IV) and/or (V) above, X is the same as the linking functionality Y.

The following examples are included to provide additional guidance to those skilled in the art in practicing the claimed disclosure. The examples provided are merely representative of the present disclosure. Accordingly, the following examples are not intended to limit the disclosure, as defined in the appended claims, in any manner.

Examples in Table 1: For each of the examples listed in Table 1, the following synthetic procedure was used to prepare the catalyst with the promoters listed in Table 1. About 30 mg to about 55 mg of dry Rohm and Haas A131 resin beads (sulfonated polystyrene, cross linked with about 4% divinylbenzene) with about 4 times it's mass of molten phenol were heated at about 70° C. for about one hour. To this mixture was added a 540 mM phenol solution of the promoter, in an amount sufficient to yield a reaction mixture, which was about 1 mmole of promoter per gram of dry resin. The resulting reaction mixture was stirred for about 4 hours, after which time a portion of the phenol was removed. The resulting mixture of catalyst in phenol had a mass of about 3.5 times the mass of the initial dry resin. To demonstrate the catalytic activity of the catalyst prepared by the procedure described above, a condensation reaction was performed by feeding a solution of about 9 wt % acetone in phenol, while maintaining a reactor temperature of 70° C. in an incremental flow reactor run at a space velocity of about 2.7 mg feed/mg dry resin/hr and a liquid residence time of about 0.9 hr. After about 40 cycles of alternate feeding and reactor mixture removal, the composition in the reactor was near steady state and samples were taken and analyzed for 4,4'-isopropylidenediphenol (pp-BPA), and 4,2'-isopropylidenediphenol (o,p-BPA),) and eight other compounds known to sometimes be formed in smaller amounts. Table 1 summarizes the results by tabulating the wt % p,p-BPA produced, and the ratio of pp-BPA to o,p-BPA ("pp/op ratio") and the overall pp-BPA selectivity, which is defined as the weight % p,p-BPA as a fraction of all products measured.

TABLE 1

Formation of pp-BPA, using a 9% acetone in phenol solution, at 70° C. for 1 hour, catalyzed by Rohm & Haas A131 resin (1 meq/g, 19% neutralized), functionalized with the following attached promoters.

| attached promoter | avg pp/op ratio | avg pp-BPA selectivity | avg pp-BPA wt % | % yield | stdev pp/op ratio | stdev pp-BPA selectivity | stdev pp-BPA wt % |
|---|---|---|---|---|---|---|---|
| 2-(3'-tert-butylthiopropylthioethyl)pyridine | 46.37 | 95.75 | 24.80 | 70.1 | 1.66 | 0.01 | 0.92 |
| 2-(6'-tert-butylthiohexylthio)-pyridine | 49.12 | 95.73 | 27.86 | 78.7 | 0.36 | 0.08 | 1.38 |
| 4-(6'-tert-butylthiohexylthioethyl)pyridine | 48.59 | 95.73 | 29.94 | 84.6 | 1.58 | 0.08 | 5.21 |
| 2-(6'-tert-butylthiohexylthio)-benzothiazole | 46.19 | 95.70 | 24.33 | 68.8 | 0.78 | 0.03 | 0.23 |

TABLE 1-continued

Formation of pp-BPA, using a 9% acetone in phenol solution, at 70° C. for 1 hour, catalyzed by Rohm & Haas A131 resin (1 meq/g, 19% neutralized), functionalized with the following attached promoters.

| attached promoter | avg pp/op ratio | avg pp-BPA selectivity | avg pp-BPA wt % | % yield | stdev pp/op ratio | stdev pp-BPA selectivity | stdev pp-BPA wt % |
|---|---|---|---|---|---|---|---|
| 2-(4'-tert-butylthiobutylthio)-pyridine | 47.31 | 95.65 | 26.30 | 74.3 | 0.34 | 0.01 | 0.34 |
| 2-(5'-tert-butylthiopentylthio)-benzothiazole | 47.28 | 95.65 | 25.95 | 73.3 | 2.06 | 0.03 | 2.34 |
| 4-(4'-tert-butylthiobutylthioethyl)pyridine | 48.67 | 95.65 | 25.96 | 73.4 | 0.62 | 0.10 | 0.52 |
| 4-(5'-tert-butylthiopentylthioethyl)pyridine | 45.27 | 95.62 | 27.96 | 79.0 | 0.40 | 0.08 | 2.87 |
| 2-(5'-tert-butylthiopentylthio)-pyridine | 51.42 | 95.62 | 27.71 | 78.3 | 1.17 | 0.02 | 0.16 |
| 2-(3'-tert-butylthiopropylthio)pyridine | 41.58 | 95.53 | 23.71 | 67.0 | 1.02 | 0.01 | 0.51 |
| 4-(3'-tert-butylthiopropylthioethyl)pyridine | 46.01 | 95.50 | 23.24 | 65.7 | 0.26 | 0.03 | 1.49 |
| 1-methyl-2-(3'-tert-butylthiopropylthio)imidazole | 41.85 | 95.42 | 21.99 | 62.2 | 0.86 | 0.03 | 0.47 |
| 4-(3'-tert-butylthiopropylthio)pyridine | 39.18 | 95.39 | 21.34 | 60.3 | 0.18 | 0.05 | 0.14 |
| 2-(6'-tert-butylthiohexylthio)-benzimidazole | 44.49 | 95.39 | 23.97 | 67.7 | 0.73 | 0.00 | 0.04 |
| 2-(4'-tert-butylthiobutylthio)-benzothiazole | 40.02 | 95.38 | 22.48 | 63.5 | 0.01 | 0.00 | 1.17 |
| 2-(5'-tert-butylthiopentylthio)-benzimidazole | 45.41 | 95.34 | 22.65 | 64.0 | 0.31 | 0.07 | 1.54 |
| 6-ethoxy-2-(3'-tert-butylthiopropylthio)benzothiazole | 38.11 | 95.31 | 21.63 | 61.1 | 1.16 | 0.14 | 0.28 |
| 2-(4'-tert-butylthiobutylthio)-benzimidazole | 42.77 | 95.29 | 23.53 | 66.5 | 2.59 | 0.00 | 8.95 |
| 2-(3'-tert-butylthiopropylthio)benzothiazole | 37.64 | 95.19 | 21.95 | 62.0 | 0.63 | 0.05 | 0.87 |
| 2-(3'-tert-butylthiopropylthio)benzimidazole | 38.40 | 95.12 | 22.09 | 62.4 | 0.64 | 0.01 | 1.56 |
| 4-tert-butyl-thiomethylbenzyl amine, carbon dioxide complex | 38.50 | 95.06 | 23.52 | 66.5 | 1.47 | 0.00 | 0.64 |
| 5-methyl-2-(3'-tert-butylthiopropylthio)benzimidazole hydrochloride | 37.37 | 95.05 | 22.17 | 62.7 | 0.52 | 0.09 | 0.23 |
| 4-pyridyl ethyl mercaptan | 33.82 | 94.98 | 22.64 | 64.0 | 0.26 | 0.14 | 1.39 |
| 2-(2'-tert-butylthioethyl)pyridine | 32.07 | 94.85 | 26.89 | 76.0 | 0.53 | 0.11 | 0.30 |
| 5-mercaptopentylamine hydrochloride | 38.10 | 94.82 | 27.18 | 76.8 | 0.55 | 0.52 | 0.16 |
| 1-(3'-tert-butylthiopropyl)-1,3-dihydro-benzimidazole-2-one | 27.21 | 94.13 | 21.50 | 60.8 | 0.82 | 0.08 | 1.47 |
| 4-tert-butyl-thiomethylbenzyl triethyl ammonium chloride | 24.58 | 93.90 | 18.77 | 53.1 | 0.03 | 0.10 | 0.30 |

From the results presented in Table 1, it is evident that the catalysts prepared by the method of the present disclosure using the attached promoters listed in Table 1, can effectively catalyze the formation of pp-BPA from phenol and acetone. For comparison, when Rohm and Haas A131 resin beads are used under similar conditions as described above, but without an attached promoter, the p,p-BPA produced amounts to about 9.9 wt %, with app selectivity of about 83.8%, and app/op ratio of about 7.5. Furthermore, when Rohm and Haas A131 resin beads are used under similar conditions as described above, except with a tert-butoxy carbonyl sulfur protected cysteamine promoter, the p,p-BPA produced amounts to about 22.5 wt %, with app selectivity of about 93.7%, and app/op ratio of about 23.9.

While the disclosure has been illustrated and described, it is not intended to be limited to the details shown, since various modifications and substitutions can be made without departing in any way from the spirit of the present invention. As such, further modifications and equivalents of the disclosure herein disclosed can occur to persons skilled in the art using no more than routine experimentation, and all such modifications and equivalents are believed to be within the spirit and scope of the disclosure as defined by the following claims.

What is claimed is:

1. A method for producing a catalyst composition which catalyzes the formation of bisphenols from aromatic hydroxy compounds and carbonyl containing compounds, said method comprising the step of attaching a poly-sulfur mercaptan promoter component to a solid acid support component comprising a protic acid functionality, said poly-sulfur mercaptan promoter component having the following structure (I), $$R_1 \pqty{ \pqty{(X)_a-S}_b-(Y)_c-S-R_2 }_d \quad (I)$$

wherein $R_1$ is a functionality selected from the group consisting of a positively charged ammonium functionality, a positively charged guanidinium functionality and a positively charged phosphonium functionality;

wherein a is between about 0 and about 11;

wherein b is between about 1 and about 11;

wherein c is between about 1 and about 11;

wherein d is between about 1 and about 5;

wherein X is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms;

wherein Y is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms; and wherein $R_2$ is one member selected from the group consisting of a hydrogen, a secondary aliphatic functionality, a tertiary aliphatic functionality, an ester functionality, a carbonate functionality, and a benzyl functionality which is attached via the benzylic methylene carbon.

2. The method of claim 1, wherein said tertiary aliphatic functionality is one member selected from the group consisting of a branched aliphatic functionality, and a cyclic aliphatic functionality.

3. The method of claim 1, wherein said $R_2$ functionality is one member selected from the group consisting of an isopropyl functionality, an isobutyl functionality, a tertiary butyl functionality, a tertiary amyl functionality, a cyclopentyl functionality, a benzyl, a 4-methoxybenzyl functionality, a 1-methylcyclohexyl functionality, and a cyclohexyl functionality.

4. The method of claim 1, wherein said ester functionality is one member selected from the group consisting of an acetate functionality, a propionate functionality, and a benzoate functionality.

5. The method of claim 1, wherein said carbonate functionality is one member selected from the group consisting of an alkyl carbonate functionality, and an aromatic carbonate functionality.

6. The method of claim 1, wherein the bisphenol which is being formed is 4,4'-isopropylidenediphenol.

7. The method of claim 1, wherein the carbonyl containing compound is a ketone or an aldehyde.

8. The method of claim 1, wherein the aromatic hydroxy compound is phenol, and the carbonyl containing compound is acetone.

9. The method of claim 1, wherein the attachment step is performed in an aqueous solution comprising water.

10. The method of claim 1, wherein said solid acid comprises at least one member selected from the group consisting of polystyrene, a zeolite, and silica.

11. The method of claim 1, wherein said protic acid functionality comprises at least one member selected from the group consisting of a sulfonic acid functionality, a phosphonic acid functionality, and a carboxylic acid functionality.

12. The method of claim 1, wherein the linking functionality X, is the same as the linking functionality Y.

13. A method for forming bisphenols, comprising the step of reacting an aromatic hydroxy compound with a carbonyl containing compound in the presence of a catalyst composition, said catalyst composition comprising a solid acid component and a poly-sulfur mercaptan promoter component having the following structure (I),

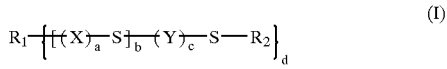
(I)

wherein $R_1$ is a functionality selected from the group consisting of a positively charged ammonium functionality, a positively charged guanidinium functionality and a positively charged phosphonium functionality;

wherein a is between about 0 and about 11;
wherein b is between about 1 and about 11;
wherein c is between about 1 and about 11;
wherein d is between about 1 and about 5;
wherein X is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms;

wherein Y is a linking functionality which is one member selected from the group consisting of a linear aliphatic chain comprising between about 1 and about 11 carbon atoms, a cyclic aliphatic ring comprising at least 5 carbon atoms, a cyclic aromatic ring comprising at least 6 carbon atoms, a cyclic aliphatic heterocycle comprising at least 3 carbon atoms, and a cyclic aromatic heterocycle comprising at least 3 carbon atoms; and wherein $R_2$ is one member selected from the group consisting of a hydrogen, a secondary aliphatic functionality, a tertiary aliphatic functionality, an ester functionality, a carbonate functionality, and a benzyl functionality which is attached via the benzylic methylene carbon.

14. The method of claim 13, wherein said tertiary aliphatic functionality is one member selected from the group consisting of a branched aliphatic functionality, and a cyclic aliphatic functionality.

15. The method of claim 13, wherein said $R_2$ is one member selected from the group consisting of a, an isopropyl functionality, an isobutyl functionality, a tertiary butyl functionality, a tertiary amyl functionality, a cyclopentyl functionality, a benzyl, a 4-methoxybenzyl, a 1-methylcyclohexyl functionality, and a cyclohexyl functionality.

16. The method of claim 13, wherein said ester functionality is one member selected from the group consisting of an acetate functionality, a propionate functionality, and a benzoate functionality.

17. The method of claim 13, wherein said carbonate functionality is one member selected from the group consisting of an alkyl carbonate functionality, and an aromatic carbonate functionality.

18. The method of claim 13, wherein the bisphenol which is being formed is 4,4'-isopropylidenediphenol.

19. The method of claim 13 wherein the aromatic hydroxy compound is phenol.

20. The method of claim 13, wherein the carbonyl containing compound is a ketone or an aldehyde.

21. The method of claim 20 wherein the ketone is acetone.

22. The method of claim 13, wherein said solid acid comprises at least one member selected from the group consisting of polystyrene, a zeolite, and silica.

23. The method of claim 13, wherein said solid acid is a sulfonic acid functionalized polymeric resin.

24. The method of claim 23, wherein said polymeric resin further comprises divinylbenzene.

25. The method of claim 24, wherein the amount of divinylbenzene is up to about 12 percent of the total weight of the polymeric resin.

26. The method of claim 13 wherein said solid acid component comprises at least one member selected from the group consisting of a sulfonic acid functionality, a phosphonic acid functionality, and a carboxylic acid functionality.

27. The method of claim 13, wherein the linking functionality X, is the same as the linking functionality Y.

* * * * *

UNITED STATES PATENT AND TRADEMARK OFFICE
CERTIFICATE OF CORRECTION

PATENT NO. : 6,872,860 B1
DATED : March 29, 2005
INVENTOR(S) : Webb et al.

It is certified that error appears in the above-identified patent and that said Letters Patent is hereby corrected as shown below:

Title page,
Item [56], References Cited, U.S. PATENT DOCUMENTS, after "4,177,350A 12/1979" delete "Zimgibl" and insert therefor -- Zimglbl --
OTHER PUBLICATIONS, "Patent Abstracts of Japan:" reference, "2001-286770 Dated" delete "Oct 16, 2000" and insert therefor -- Oct 16, 2001. --

Column 3,
Line 33, after "e.g., a", delete "Bronsted" and insert therefor -- Brönsted --

Column 10,
Line 5, before "about 11" delete "Band" and insert therefor -- and --

Column 14,
Line 45, after "isopropylidenediphenol", delete "(pp-BPA)" and insert therefor -- *(p,p-BPA)* --

Column 15,
Lines 39 and 44, after "with" delete "app"and insert therefor -- a *pp* --
Line 40, before "ratio" delete "app/op" and insert therefor -- a *pp/op* --
Line 45, before "ratio" delete "app/op"and insert therefor -- a *pp/op* --

Signed and Sealed this

Twelfth Day of July, 2005

JON W. DUDAS
*Director of the United States Patent and Trademark Office*